United States Patent
Bos et al.

(10) Patent No.: US 10,501,390 B2
(45) Date of Patent: Dec. 10, 2019

(54) ALKANE OXIDATIVE DEHYDROGENATION AND/OR ALKENE OXIDATION

(71) Applicant: SHELL OIL COMPANY, Houston, TX (US)

(72) Inventors: Alouisius Nicolaas Renée Bos, Amsterdam (NL); Ronald Jan Schoonebeek, Amsterdam (NL); Frank Spies, Amsterdam (NL); Michael Johannes Franciscus Maria Verhaak, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/322,479

(22) PCT Filed: Jun. 29, 2015

(86) PCT No.: PCT/EP2015/064638
§ 371 (c)(1),
(2) Date: Dec. 28, 2016

(87) PCT Pub. No.: WO2016/001111
PCT Pub. Date: Jan. 7, 2016

(65) Prior Publication Data
US 2017/0137347 A1 May 18, 2017

(30) Foreign Application Priority Data
Jun. 30, 2014 (EP) ..................... 14174921

(51) Int. Cl.
*C07C 5/48* (2006.01)
*B01J 27/057* (2006.01)
*B01J 37/03* (2006.01)
*B01J 37/06* (2006.01)
*B01J 37/08* (2006.01)
*B01J 35/02* (2006.01)
*B01J 37/00* (2006.01)
*B01J 37/02* (2006.01)
*B01J 37/04* (2006.01)

(52) U.S. Cl.
CPC ............ *C07C 5/48* (2013.01); *B01J 27/0576* (2013.01); *B01J 35/023* (2013.01); *B01J 35/026* (2013.01); *B01J 37/0036* (2013.01); *B01J 37/0236* (2013.01); *B01J 37/031* (2013.01); *B01J 37/04* (2013.01); *B01J 37/06* (2013.01); *B01J 37/08* (2013.01); *B01J 2523/00* (2013.01); *C07C 2523/28* (2013.01); *C07C 2523/847* (2013.01); *C07C 2527/057* (2013.01); *Y02P 20/52* (2015.11)

(58) Field of Classification Search
CPC ............... B01J 2523/00; B01J 2523/55; B01J 2523/56; B01J 2523/64; B01J 2523/68; B01J 27/0576; B01J 35/023; B01J 35/026; B01J 37/0036; B01J 37/0236; B01J 37/031; B01J 37/04; B01J 37/06; B01J 37/08; C07C 5/48; C07C 11/04; C07C 2523/28; C07C 2523/847; C07C 2527/057
See application file for complete search history.

(56) References Cited

U.S. PATENT DOCUMENTS

| | | | |
|---|---|---|---|
| 4,899,003 A * | 2/1990 | Manyik | C07C 5/48 585/313 |
| 7,091,377 B2 | 8/2006 | Borgmeier et al. | |
| 2003/0158440 A1 | 8/2003 | Zeyss et al. | |
| 2004/0063989 A1 * | 4/2004 | Hechler | C07C 51/215 558/320 |
| 2004/0082190 A1 | 4/2004 | Borgmeier et al. | |
| 2009/0287019 A1 | 11/2009 | Hazin et al. | |

FOREIGN PATENT DOCUMENTS

| | | |
|---|---|---|
| WO | 2003064035 | 8/2003 |
| WO | 2010096909 | 9/2010 |

OTHER PUBLICATIONS

International Search Report dated Aug. 5, 2015 of PCT/EP2015/064638 filed Jun. 29, 2015.

* cited by examiner

*Primary Examiner* — Sharon Pregler

(57) ABSTRACT

The invention relates to a process of the oxidative dehydrogenation of an alkane containing 2 to 6 carbon atoms and/or the oxidation of an alkene containing 2 to 6 carbon atoms, comprising contacting a first gas stream comprising oxygen and the alkane containing 2 to 6 carbon atoms and/or the alkene containing 2 to 6 carbon atoms with a mixed metal oxide catalyst containing molybdenum, vanadium, niobium and optionally tellurium; followed by contacting a second gas stream comprising methane, an inert gas or oxygen or any combination of two or more of these with the catalyst, wherein the second gas stream comprises 0 to 25 vol. % of the alkane containing 2 to 6 carbon atoms and/or alkene containing 2 to 6 carbon atoms.

11 Claims, No Drawings

ALKANE OXIDATIVE DEHYDROGENATION AND/OR ALKENE OXIDATION

PRIORITY CLAIM

The present application is the National Stage (§ 371) of International Application No. PCT/EP2015/064638, filed Jun. 29, 2015, which claims priority from European Patent Application No. 14174921.8, filed Jun. 30, 2014 which is incorporated herein by reference.

FIELD OF THE INVENTION

The present invention relates to a process of alkane oxidative dehydrogenation (oxydehydrogenation; ODH) and/or alkene oxidation.

BACKGROUND OF THE INVENTION

It is known to oxidatively dehydrogenate alkanes, such as alkanes containing 2 to 6 carbon atoms, for example ethane or propane resulting in ethylene and propylene, respectively, in an oxidative dehydrogenation (oxydehydrogenation; ODH) process. Examples of alkane ODH processes, including catalysts and other process conditions, are for example disclosed in U.S. Pat. No. 7,091,377, WO2003064035, US20040147393, WO2010096909 and US20100256432. Mixed metal oxide catalysts containing molybdenum (Mo), vanadium (V), niobium (Nb) and optionally tellurium (Te) as the metals, can be used as such oxydehydrogenation catalysts. Such catalysts may also be used in the direct oxidation of alkenes to carboxylic acids, such as in the oxidation of alkenes containing 2 to 6 carbon atoms, for example ethylene or propylene resulting in acetic acid and acrylic acid, respectively.

It is an objective of the present invention to provide an alkane ODH and/or alkene oxidation process, wherein a mixed metal oxide catalyst containing Mo, V, Nb and optionally Te is used, wherein said alkane ODH and/or alkene oxidation process is terminated in such way that the activity and/or selectivity of said mixed metal oxide catalyst in a subsequent alkane ODH and/or alkene oxidation process is maintained.

SUMMARY OF THE INVENTION

Surprisingly it was found that such termination of an alkane ODH and/or alkene oxidation process, wherein the alkane and/or alkene contains 2 to 6 carbon atoms, such as ethane, propane, ethylene and/or propylene, as described above, can be achieved by contacting a gas stream comprising methane, an inert gas or oxygen or any combination of two or more of these with the mixed metal oxide catalyst containing molybdenum, vanadium, niobium and optionally tellurium, wherein said gas stream comprises 0 to 25 vol. % of the alkane containing 2 to 6 carbon atoms and/or alkene containing 2 to 6 carbon atoms.

Accordingly, the present invention relates to a process of the oxidative dehydrogenation of an alkane containing 2 to 6 carbon atoms and/or the oxidation of an alkene containing 2 to 6 carbon atoms, comprising contacting a first gas stream comprising oxygen and the alkane containing 2 to 6 carbon atoms and/or the alkene containing 2 to 6 carbon atoms with a mixed metal oxide catalyst containing molybdenum, vanadium, niobium and optionally tellurium; followed by contacting a second gas stream comprising methane, an inert gas or oxygen or any combination of two or more of these with the catalyst, wherein the second gas stream comprises 0 to 25 vol. % of the alkane containing 2 to 6 carbon atoms and/or alkene containing 2 to 6 carbon atoms.

Surprisingly, it has appeared that by terminating the alkane ODH and/or alkene oxidation process in this way, the activity and/or selectivity of the mixed metal oxide catalyst in a subsequent alkane ODH and/or alkene oxidation process is not only maintained, but may even be increased advantageously.

Further, in addition to maintaining the activity and/or selectivity of the catalyst, it has appeared that when terminating an alkane ODH and/or alkene oxidation step by the termination method of the present invention, the temperature need not be reduced. Normally, when terminating a reaction step, the temperature would have to be reduced by taking measures to cool down the reactor. Such cooling down costs time which results in that more time lapses before the same catalyst can be used again in a next reaction step. In the present invention, even when no such measures are taken to cool down, the activity and/or selectivity of the mixed metal oxide catalyst in a subsequent alkane ODH and/or alkene oxidation step is maintained and may even be increased. Therefore, the present termination method, surprisingly, has the additional advantage that termination may be performed relatively quickly without having to cool down the reactor.

DETAILED DESCRIPTION OF THE INVENTION

While the process of the present invention and the gas stream or gas streams used in said process are described in terms of "comprising", "containing" or "including" one or more various described steps and components, respectively, they can also "consist essentially of" or "consist of" said one or more various described steps and components, respectively.

The present invention is a process of the oxidative dehydrogenation of an alkane containing 2 to 6 carbon atoms and/or the oxidation of an alkene containing 2 to 6 carbon atoms, including a method of terminating such process. Firstly, the alkane oxidative dehydrogenation and/or alkene oxidation process as such is discussed in more detail hereinbelow, followed by a more detailed discussion of the termination method.

In the present process, a gas stream comprising oxygen ($O_2$) and an alkane containing 2 to 6 carbon atoms and/or an alkene containing 2 to 6 carbon atoms is contacted with a mixed metal oxide catalyst containing molybdenum, vanadium, niobium and optionally tellurium. Within the present specification, said gas stream comprising oxygen and an alkane containing 2 to 6 carbon atoms and/or an alkene containing 2 to 6 carbon atoms is also referred to as "first gas stream".

Preferably, in said alkane oxidative dehydrogenation process and/or alkene oxidation process, that is to say during contacting the first gas stream with said catalyst, the temperature is of from 300 to 500° C. More preferably, said temperature is of from 310 to 450° C., more preferably of from 320 to 420° C., most preferably of from 330 to 420° C.

Preferably, said temperature is at least 310° C., more preferably at least 320° C., more preferably at least 330° C., more preferably at least 340° C., more preferably at least 345° C., more preferably at least 350° C., more preferably at least 355° C., most preferably at least 360° C.

Further, preferably, said temperature is at most 480° C., more preferably at most 460° C., more preferably at most 450° C., more preferably at most 440° C., more preferably at most 430° C., more preferably at most 420° C., more preferably at most 410° C., most preferably at most 400° C.

Still further, in said alkane oxidative dehydrogenation process and/or alkene oxidation process of the present invention, that is to say during contacting the first gas stream with said catalyst, typical pressures are 0.1-20 bara (i.e. "bar absolute"). Further, in a preferred embodiment, said pressure is of from 0.1 to 15 bara, more preferably of from 0.5 to 10 bara, most preferably of from 1 to 5 bara.

In the present invention, preferably, one gas stream comprising oxygen and the alkane and/or alkene is fed to the reactor as the first gas stream. Alternatively, two or more gas streams may be fed to the reactor, which gas streams form a combined gas stream inside the reactor. For example, one gas stream comprising oxygen and another gas stream comprising an alkane, such as ethane, may be fed to the reactor separately.

Preferably, in the alkane oxidative dehydrogenation process of the present invention, the alkane containing 2 to 6 carbon atoms is a linear alkane in which case said alkane may be selected from the group consisting of ethane, propane, butane, pentane and hexane. Further, preferably, said alkane contains 2 to 4 carbon atoms and is selected from the group consisting of ethane, propane and butane. More preferably, said alkane is ethane or propane. Most preferably, said alkane is ethane.

Further, preferably, in the alkene oxidation process of the present invention, the alkene containing 2 to 6 carbon atoms is a linear alkene in which case said alkene may be selected from the group consisting of ethylene, propylene, butene, pentene and hexene. Further, preferably, said alkene contains 2 to 4 carbon atoms and is selected from the group consisting of ethylene, propylene and butene. More preferably, said alkene is ethylene or propylene.

The product of said alkane oxidative dehydrogenation process may comprise the dehydrogenated equivalent of the alkane, that is to say the corresponding alkene. For example, in the case of ethane such product may comprise ethylene, in the case of propane such product may comprise propylene, and so on. Such dehydrogenated equivalent of the alkane is initially formed in said alkane oxidative dehydrogenation process. However, in said same process, said dehydrogenated equivalent may be further oxidized under the same conditions into the corresponding carboxylic acid which may or may not contain one or more unsaturated double carbon-carbon bonds. As mentioned above, it is preferred that the alkane containing 2 to 6 carbon atoms is ethane or propane. In the case of ethane, the product of said alkane oxidative dehydrogenation process may comprise ethylene and/or acetic acid, preferably ethylene. Further, in the case of propane, the product of said alkane oxidative dehydrogenation process may comprise propylene and/or acrylic acid, preferably acrylic acid.

The product of said alkene oxidation process comprises the oxidized equivalent of the alkene. Preferably, said oxidized equivalent of the alkene is the corresponding carboxylic acid. Said carboxylic acid may or may not contain one or more unsaturated double carbon-carbon bonds. As mentioned above, it is preferred that the alkene containing 2 to 6 carbon atoms is ethylene or propylene. In the case of ethylene, the product of said alkene oxidation process may comprise acetic acid. Further, in the case of propylene, the product of said alkene oxidation process may comprise acrylic acid.

Additionally, the first gas stream comprising oxygen and the alkane and/or alkene may contain an inert gas. Said inert gas may be selected from the group consisting of the noble gases and nitrogen ($N_2$). Preferably, the inert gas is nitrogen or argon, more preferably nitrogen. Said oxygen is an oxidizing agent, thereby resulting in oxidative dehydrogenation of the alkane and/or oxidation of the alkene. Said oxygen may originate from any source, such as for example air.

Ranges for the molar ratio of oxygen to the alkane and/or alkene in the first gas stream which are suitable, are of from 0.01 to 1, more suitably 0.05 to 0.5. Said gas stream may comprise more than 25 vol. % of the alkane and/or alkene, suitably at least 30 vol. %, more suitably at least 40 vol. %, most suitably at least 50 vol. %. Further, said gas stream may comprise at most 90 vol. % of the alkane and/or alkene, suitably at most 80 vol. %, more suitably at most 70 vol. %. Furthermore, in a preferred embodiment, said gas stream comprises 5 to 35 vol. % of oxygen, more suitably 15 to 30 vol. % of oxygen, and 40 to 80 vol. % of the alkane and/or alkene, more suitably 50 to 70 vol. % of the alkane and/or alkene, and less than 80 (0 to 80) vol. % of the above-mentioned inert gas, more suitably less than 50 (0 to 50) vol. % of said inert gas, more suitably 5 to 35 vol. % of said inert gas, most suitably 10 to 20 vol. % of said inert gas.

In the context of the present invention, in a case where a gas stream comprises two or more components, these components are to be selected in an overall amount not to exceed 100 vol. %.

Said ratio of oxygen to the alkane and/or alkene and said volume percentages for oxygen, the alkane and/or alkene and said inert gas are the ratio and volume percentages, respectively, before the gas stream is contacted with the catalyst. Obviously, after contact with the catalyst, at least part of the oxygen and alkane and/or alkene from the gas stream gets consumed.

Preferably, the first gas stream comprises no or substantially no inert gas.

Within the present specification, by "substantially no" in relation to the amount of a specific component in a gas stream, it is meant an amount which is at most 10,000, preferably at most 5,000, more preferably at most 1,000, more preferably at most 500, more preferably at most 100, more preferably at most 50, more preferably at most 30, more preferably at most 20, and most preferably at most 10 ppmv (parts per million by volume) of the component in question, based on the amount (i.e. volume) of said gas stream.

Preferably, in the present invention, the mixed metal oxide catalyst containing molybdenum, vanadium, niobium and optionally tellurium is a heterogeneous catalyst.

In the present invention, the catalyst is a mixed metal oxide catalyst containing molybdenum, vanadium, niobium and optionally tellurium as the metals, which catalyst may have the following formula:

$$Mo_1V_aTe_bNb_cO_n$$

wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for O) is a number which is determined by the valency and frequency of elements other than oxygen.

Examples of oxydehydrogenation processes, including catalysts and other process conditions, are for example disclosed in above-mentioned U.S. Pat. No. 7,091,377, WO2003064035, US20040147393, WO2010096909 and US20100256432, the disclosures of which are herein incorporated by reference.

The amount of the catalyst in said process is not essential. Preferably, a catalytically effective amount of the catalyst is used, that is to say an amount sufficient to promote the alkane oxydehydrogenation and/or alkene oxidation reaction.

In general, the product stream comprises water in addition to the desired product. Water may easily be separated from said product stream, for example by cooling down the product stream from the reaction temperature to a lower temperature, for example room temperature, so that the water condenses and can then be separated from the product stream.

Hereinbelow, the termination method as part of the present process, which method follows after the above-discussed alkane oxydehydrogenation and/or alkene oxidation step, is discussed in more detail. Said termination method comprises contacting a second gas stream comprising methane, an inert gas or oxygen or any combination of two or more of these with the catalyst. Within the present specification, said gas stream comprising methane, an inert gas or oxygen or any combination of two or more of these is also referred to as "second gas stream".

In the present invention, the second gas stream comprises 0 to 25 vol. % of the alkane containing 2 to 6 carbon atoms and/or alkene containing 2 to 6 carbon atoms.

Preferably, the second gas stream comprises no or substantially no alkane containing 2 to 6 carbon atoms and/or alkene containing 2 to 6 carbon atoms.

In a case wherein in said termination method the second gas stream also comprises an alkane containing 2 to 6 carbon atoms and/or alkene containing 2 to 6 carbon atoms, the amount of said alkane and/or alkene containing 2 to 6 carbon atoms may be 1 to 25 vol. % or 1 to 10 vol. % or 1 to 5 vol. %.

As mentioned above, the second gas stream may comprise an inert gas. Said inert gas may be selected from the group consisting of the noble gases and nitrogen ($N_2$). Preferably, the inert gas is nitrogen or argon, more preferably nitrogen.

Further, in case the second gas stream comprises a combination of methane and an inert gas, the volume ratio of methane to inert gas may vary within broad ranges and may be of from 100:1 to 1:100, more suitably 20:1 to 1:20, most suitably 10:1 to 1:10.

Still further, in case the second gas stream comprises no combination of methane and an inert gas, the second gas stream either comprises methane and no or substantially no inert gas or comprises an inert gas and no or substantially no methane.

In said termination method, the second gas stream may comprise an amount of methane of from 0 to 100 vol. %, more suitably 0 to 99 vol. %, more suitably 0 to 95 vol. %, more suitably 0 to 90 vol. %, more suitably 0 to 70 vol. %, most suitably 0 to 50 vol. %; an amount of an inert gas of from 0 to 100 vol. %, more suitably 0 to 99 vol. %, more suitably 0 to 95 vol. %, more suitably 0 to 90 vol. %, more suitably 0 to 70 vol. %, most suitably 0 to 50 vol. %; and an amount of oxygen of from 0 to 100 vol. %, more suitably 0 to 99 vol. %, more suitably 0 to 95 vol. %, more suitably 0 to 90 vol. %, more suitably 0 to 70 vol. %, most suitably 0 to 50 vol. %.

Further, in said termination method, the second gas stream may comprise methane in an amount of 0 vol. %, more suitably at least 1 vol. %, more suitably at least 5 vol. %, more suitably at least 10 vol. %, most suitably at least 30 vol. %, and at most 100 vol. %, more suitably at most 99 vol. %, more suitably at most 95 vol. %, more suitably at most 90 vol. %, most suitably at most 70 vol. %.

Further, in said termination method, the second gas stream may comprise an inert gas in an amount of 0 vol. %, more suitably at least 1 vol. %, more suitably at least 5 vol. %, more suitably at least 10 vol. %, most suitably at least 30 vol. %, and at most 100 vol. %, more suitably at most 99 vol. %, more suitably at most 95 vol. %, more suitably at most 90 vol. %, most suitably at most 70 vol. %.

Further, in said termination method, the second gas stream may comprise oxygen in an amount of 0 vol. %, more suitably at least 1 vol. %, more suitably at least 5 vol. %, more suitably at least 10 vol. %, most suitably at least 30 vol. %, and at most 100 vol. %, more suitably at most 99 vol. %, more suitably at most 95 vol. %, more suitably at most 90 vol. %, most suitably at most 70 vol. %.

For example, in said termination method, the second gas stream may be a gas stream consisting of oxygen, which means that it contains no or substantially no methane and no or substantially no inert gas, preferably no or substantially no component other than oxygen.

However, preferably, in one embodiment of said termination method, the second gas stream comprises methane and/or an inert gas and no or substantially no oxygen, which embodiment is herein referred to as "Embodiment A". That is to say, in Embodiment A, the second gas stream comprises methane, an inert gas or a combination of methane and an inert gas, but the second gas stream comprises no or substantially no oxygen.

In said Embodiment A of the termination method, the second gas stream may comprise methane and/or an inert gas in an amount of from 60 to 100 vol. %, more suitably 75 to 100 vol. %, more suitably 90 to 100 vol. %, more suitably 95 to 100 vol. %, most suitably 99 to 100 vol. %. Further, in said Embodiment A, the second gas stream may be a gas stream consisting of methane and/or an inert gas, which means that it contains no or substantially no oxygen, in particular no or substantially no component other than methane and/or inert gas.

Further, preferably, in another embodiment of said termination method, the second gas stream comprises oxygen and methane and/or an inert gas, which embodiment is herein referred to as "Embodiment B". That is to say, in Embodiment B, the second gas stream comprises oxygen and in addition the second gas stream also comprises methane, an inert gas or a combination of methane and an inert gas.

In said Embodiment B of the termination method, the second gas stream may comprise 5 to 35 vol. % of oxygen, more suitably 15 to 30 vol. % of oxygen, and in addition the second gas stream may comprise 65 to 95 vol. % of methane and/or an inert gas, more suitably 70 to 85 vol. % of methane and/or an inert gas. Further, in case in said Embodiment B the second gas stream additionally comprises methane, ranges for the molar ratio of oxygen to methane in said gas stream which are suitable, are of from 0.01 to 1, more suitably 0.05 to 0.5. Still further, in case in said Embodiment B the second gas stream additionally comprises an inert gas, such as nitrogen, the second gas stream may be an air stream, optionally diluted with an inert gas, such as nitrogen.

Further, said termination method may comprise one step or multiple steps. Still further, said one step or at least one of said multiple steps may comprise contacting a gas stream, as described in any one of the above-mentioned embodiments for the second gas stream, with the mixed metal oxide catalyst containing molybdenum, vanadium, niobium and optionally tellurium.

For example, said termination method may comprise the following two steps: a first step comprising contacting a gas stream as described in above-mentioned Embodiment B for the second gas stream, which gas stream comprises oxygen and methane and/or an inert gas, with the catalyst, followed by a second step comprising contacting a gas stream as described in above-mentioned Embodiment A for the second gas stream, which gas stream comprises methane and/or an inert gas and no or substantially no oxygen, with the catalyst.

Preferably, during said termination method, the temperature is of from 300 to 500° C. More preferably, said temperature is of from 310 to 450° C., more preferably of from 320 to 420° C., most preferably of from 330 to 420° C.

Preferably, said temperature is at least 310° C., more preferably at least 320° C., more preferably at least 330° C., more preferably at least 340° C., more preferably at least 345° C., more preferably at least 350° C., more preferably at least 355° C., most preferably at least 360° C.

Further, preferably, said temperature is at most 480° C., more preferably at most 460° C., more preferably at most 450° C., more preferably at most 440° C., more preferably at most 430° C., more preferably at most 420° C., more preferably at most 410° C., most preferably at most 400° C.

Still further, during said termination method, typical pressures are 0.1-20 bara (i.e. "bar absolute"). Further, in a preferred embodiment, said pressure is of from 0.1 to 15 bara, more preferably of from 0.5 to 10 bara, most preferably of from 1 to 5 bara.

The time period for said termination method may vary within wide ranges and may be of from 10 minutes to 10 hours, more suitably of from 30 minutes to 5 hours.

Further, preferably, during the entire process, comprising said alkane oxydehydrogenation and/or alkene oxidation step and said termination method, the level of external heating is maintained constant and no external cooling down is effected. Still further, preferably, the temperature during the entire process falls within the above-mentioned temperature ranges. Likewise, preferably, the pressure during the entire process falls within the above-mentioned pressure ranges.

The invention is further illustrated by the following Examples.

EXAMPLES (A) Preparation of the Catalyst

A mixed metal oxide catalyst containing molybdenum (Mo), vanadium (V), niobium (Nb) and tellurium (Te) was prepared, for which catalyst the molar ratio of said 4 metals was $Mo_1V_{0.29}Nb_{0.17}Te_{0.12}$.

Two solutions were prepared. Solution 1 was obtained by dissolving 15.8 g of ammonium niobate oxalate and 4.0 g of anhydrous oxalic acid in 160 ml of water at room temperature. Solution 2 was prepared by dissolving 35.6 g of ammonium heptamolybdate, 6.9 g of ammonium metavanadate and 5.8 g of telluric acid ($Te(OH)_6$) in 200 ml of water at 70° C. 7.0 g of concentrated nitric acid was then added to solution 2. The 2 solutions were combined which yielded an orange gel-like precipitate. The mixture was evaporated to dryness with the aid of a rotating evaporator ("rotavap") at 50° C.

The dried material was further dried in static air at 120° C. for 16 hours, milled to a fine powder and then calcined in static air at a temperature of 300° C. for 5 hours. After the air calcination, the material was further calcined in a nitrogen ($N_2$) stream at 600° C. for 2 hours. Then the material was treated with an aqueous 5% oxalic acid solution at 80° C. and filtered and dried at 120° C.

The dried catalyst powder was pressed into pills which pills were then milled. The milled material was then sieved using a sieve having a mesh size of 40-80 mesh. The sieved material, having a size of 40-80 mesh and composed of porous catalyst particles, was then used in the ethane oxidative dehydrogenation experiments described below.

(B) Catalytic Oxidative Dehydrogenation of Ethane and Subsequent Termination

Example 1

In Example 1, the catalyst thus prepared was used in an experiment involving ethane oxidative dehydrogenation (ethane ODH) within a small-scale testing unit comprising a vertically oriented, cylindrical, quartz reactor having an inner diameter of 3.0 mm. 0.65 g of the catalyst was loaded in the reactor. The catalyst bed height was 6 cm. On top of the catalyst bed, another bed having a height of 8 cm was placed which latter bed contained inert silicon carbide (SiC) particles having an average diameter of 0.8 mm.

In this experiment, a gas stream comprising 63 vol. % of ethane, 21 vol. % of oxygen ($O_2$) and 16 vol. % of nitrogen ($N_2$) was fed to the top of the reactor and then sent downwardly through the catalyst bed to the bottom of the reactor. Said gas stream was a combined gas stream comprising a flow of ethane having a rate of 3.00 Nl/hr, a flow of oxygen having a rate of 1.00 Nl/hr and a flow of nitrogen having a rate of 0.77 Nl/hr. "Nl" stands for "normal litre" as measured at standard temperature and pressure, namely 32° F. (0° C.) and 1 bara (100 kPa). The pressure in the reactor was 2.5 bara. The reactor was heated such that the temperature of the catalyst (at the top of the catalyst bed) was 390° C. This condition was maintained for 8 hours. This time period of 8 hours is herein referred to as "reaction period A". Directly after reaction period A, the following sequence of steps was performed:

1. The flow of ethane was gradually stopped and at the same time gradually replaced by a flow of methane having a rate of 3.00 Nl/hr, within a period of time of 3 minutes.

2. The thus obtained condition, comprising a flow of methane having a rate of 3.00 Nl/hr, a flow of oxygen having a rate of 1.00 Nl/hr and a flow of nitrogen having a rate of 0.77 Nl/hr, was maintained for 2 hours. The temperature of the catalyst decreased from 390° C. to 380° C.

3. The flow of oxygen was gradually stopped, within a period of time of 1 minute.

4. The thus obtained condition, comprising a flow of methane having a rate of 3.00 Nl/hr and a flow of nitrogen having a rate of 0.77 Nl/hr, was maintained for 1 hour.

5. A flow of oxygen having a rate of 1.00 Nl/hr was gradually introduced, within a period of time of 1 minute.

6. A flow of ethane having a rate of 3.00 Nl/hr was gradually introduced and at the same time the flow of methane was gradually stopped, within a period of time of 3 minutes.

7. The thus obtained condition, comprising a flow of ethane having a rate of 3.00 Nl/hr, a flow of oxygen having a rate of 1.00 Nl/hr and a flow of nitrogen having a rate of 0.77 Nl/hr, was maintained for 8 hours. This time period of 8 hours is herein referred to as "reaction period B".

The conversion of ethane and the product composition were measured with a gas chromatograph (GC) equipped with a thermal conductivity detector (TCD) and with another GC equipped with a flame ionization detector. Acetic acid by-product and water from the reaction were trapped in a quench pot.

In Table 1 below, the experimental results (conversion of ethane and selectivity towards ethylene) for Example 1 are shown.

TABLE 1

| Time | Conversion of ethane (%) | Selectivity to ethylene (%) |
| --- | --- | --- |
| 4 hours after start of reaction period A | 44 | 94 |
| 4 hours after start of reaction period B | 47 | 93 |

Comparative Example 1

In Comparative Example 1, the procedure of Example 1 was repeated with the proviso that directly after reaction period A, the following sequence of steps was performed:

1. The flow of oxygen was gradually stopped, within a period of time of 1 minute.
2. The thus obtained condition, comprising a flow of ethane having a rate of 3.00 Nl/hr and a flow of nitrogen having a rate of 0.77 Nl/hr, was maintained for 1 hour. The temperature of the catalyst decreased from 390° C. to 380° C.
3. A flow of oxygen having a rate of 1.00 Nl/hr was gradually introduced, within a period of time of 1 minute.
4. The thus obtained condition, comprising a flow of ethane having a rate of 3.00 Nl/hr, a flow of oxygen having a rate of 1.00 Nl/hr and a flow of nitrogen having a rate of 0.77 Nl/hr, was maintained for 8 hours. This time period of 8 hours is herein referred to as "reaction period B".

In Table 2 below, the experimental results (conversion of ethane and selectivity towards ethylene) for Comparative Example 1 are shown.

TABLE 2

| Time | Conversion of ethane (%) | Selectivity to ethylene (%) |
| --- | --- | --- |
| 4 hours after start of reaction period A | 44 | 93 |
| 4 hours after start of reaction period B | 24 | 94 |

Surprisingly, it appears from comparing Table 1 (Example 1) and Table 2 (Comparative Example 1) that by a termination method in accordance with the present invention (in these examples terminating an ethane ODH process), the conversion in a subsequent reaction step (said reaction period B) was not reduced when compared to the conversion in the first reaction step (said reaction period A), whereas such reduction was observed in Comparative Example 1. For Comparative Example 1, compare the reduced conversion of 24% in reaction period B with the conversion of 44% in reaction period A. Not only has it appeared that the conversion was not reduced in Example 1, but surprisingly, the conversion was actually substantially increased. For Example 1, compare the increased conversion of 47% in reaction period B with the conversion of 44% in reaction period A.

That which is claimed is:

1. A process of the oxidative dehydrogenation of an alkane containing 2 to 6 carbon atoms and/or the oxidation of an alkene containing 2 to 6 carbon atoms, comprising
    contacting a first gas stream comprising oxygen and the alkane containing 2 to 6 carbon atoms and/or the alkene containing 2 to 6 carbon atoms with a mixed metal oxide catalyst containing molybdenum, vanadium, niobium and optionally tellurium; followed by
    contacting a second gas stream comprising methane with the catalyst, wherein the second gas stream comprises no or substantially no alkane containing 2 to 6 carbon atoms and no or substantially no alkene containing 2 to 6 carbon atoms, followed by
    stopping the contacting of the first gas stream while continuing the contacting the second gas stream.

2. The process according to claim 1, wherein the temperature during the entire process is of from 300 to 500° C.

3. The process according to claim 2, wherein the temperature during the entire process is of from 310 to 450° C.

4. The process according to claim 1, wherein the pressure during the entire process is of from 0.1 to 15 bara.

5. The process according to claim 1, wherein the process is a process of the oxidative dehydrogenation of an alkane containing 2 to 6 carbon atoms and wherein said alkane is ethane or propane.

6. The process according to claim 1, wherein the process is a process of the oxidation of an alkene containing 2 to 6 carbon atoms and wherein said alkene is ethylene or propylene.

7. The process according to claim 1, wherein the contacting the first gas stream is done at a first temperature and the contacting the second gas stream is done at a second temperature less than the first temperature.

8. The process according to claim 1, further comprising stopping the contacting of the second gas stream while gradually introducing the first gas stream.

9. The process according to claim 1, wherein the second gas stream further comprises an inert gas.

10. The process according to claim 1, wherein the second gas stream further comprises an inert gas and oxygen.

11. The process according to claim 1, wherein the second gas stream further comprises oxygen.

* * * * *